April 16, 1940. J. H. NICOLAS Plant Pat. 375
ROSE PLANT
Filed May 17, 1939
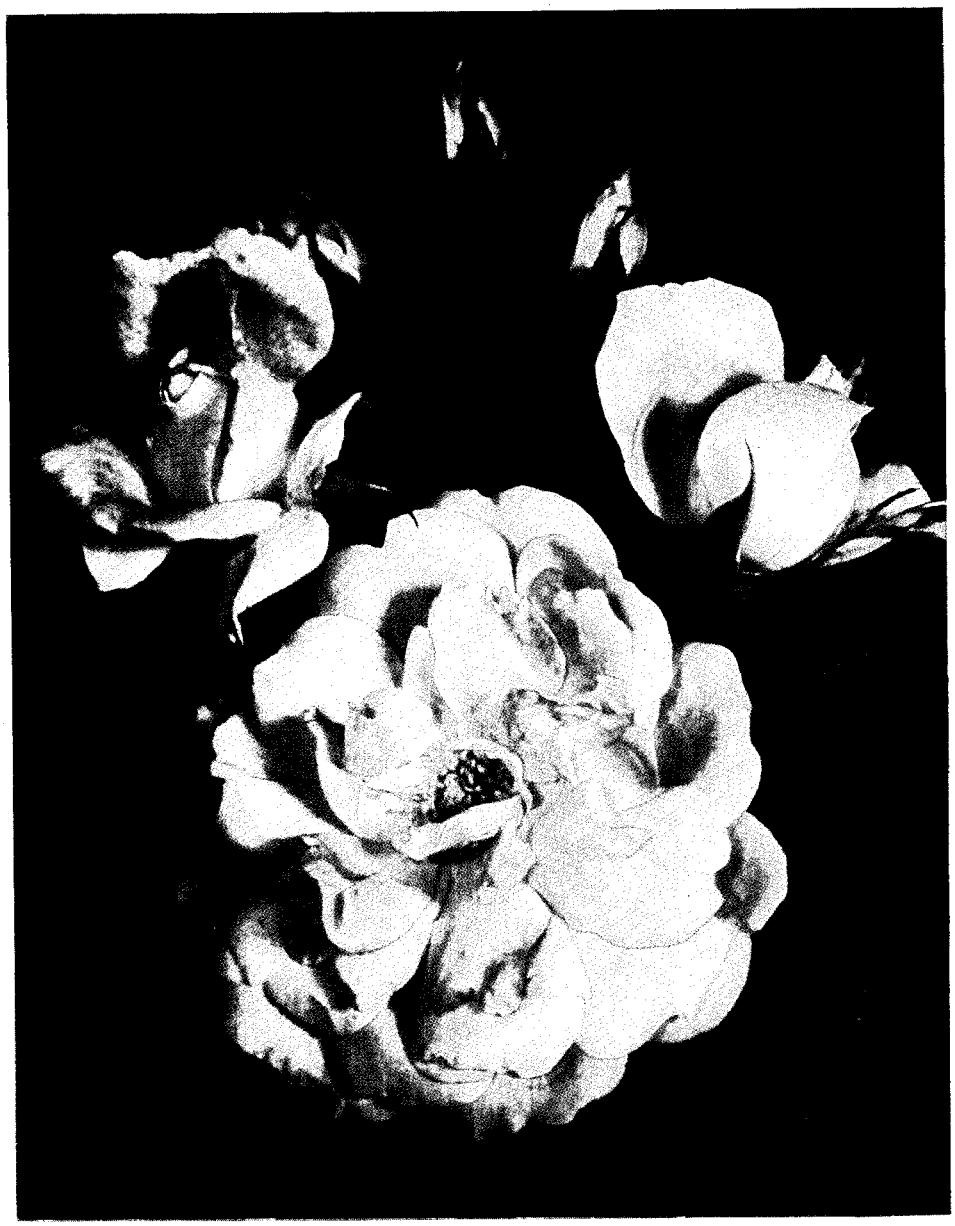
Inventor
Jean H Nicolas
By Fannie Nicolas
Administratrix of the
Estate of Jean H Nicolas
deceased
By Robb & Robb
attorneys Patented Apr. 16, 1940

UNITED STATES PATENT OFFICE

375

ROSE PLANT

Jean H. Nicolas, deceased, late of Newark, N. Y., by Fannie Nicolas, administratrix, Newark, N. Y., assignor to Jackson & Perkins Company, Newark, N. Y.

Application May 17, 1939, Serial No. 274,302

1 Claim. (Cl. 47—61)

The present invention relates to a new and distinct variety of climbing Hybrid Tea Rose plant, the result of definite efforts to combine the desirable characteristics of two well known climbers, one marked for its delicate pink flowers and the other for its yellow flowers.

This new rose was produced by crossing Mme. Gregoire Staechelin with Climbing Souvenir de Claudius Pernet, this peculiar combination developing a fragrant, remontant climbing rose of real hardiness.

The accompanying original illustration shows the flowers in approximately their actual size and in the various stages of development from bud to full open flower. The principal distinctive features are the globular form of the bud, of medium size and Cadmium Yellow when the sepals first divide; the Rose Red to Begonia Rose color of the inside and Apricot Yellow reverse of the petals of the half open flowers and in the full open flower its Empire Yellow color at the center blending into the Begonia Rose of the balance of the petals, while on the reverse the color is Pinard Yellow.

Further, the Begonia Rose color of the outer petals with the Empire Yellow aiglet, together with the shiny inside and outside of the thick informal arranged notched petals, makes a striking contrast.

The large double globular blooms of tea fragrance are borne in clusters on medium strong stems producing a decidedly attractive Begonia Rose to Eosine Pink tonality during the blooming period.

Asexual reproduction of this rose shows that the distinctive features are established.

The following is a detail description of the new variety, all references to color being in accord with Ridgway's Color Standard.

Parentage:

*Seed Parent.*—Mme. Gregoire Staechelin.

*Pollen Parent.*—Climbing Souvenir de Claudius Pernet.

Classification:

*Botanic and Commercial.*—Climber.

*Flower*

Observations made at Newark, New York, in the morning of June 30, 1938.

Blooming habit:

*Recurrent.*—Spring and fall.

Bud:

*Size.*—Medium.

*Form.*—Globular. Is not affected by wet or hot weather.

*Color.*—When sepals first divide—Cadmium Yellow, Plate 3. When petals begin to unfurl—Light Cadium, Plate 4. When half blown: inside of petals—between Rose Red, Plate 12, and Begonia Rose, Plate 1; reverse of petals—Apricot Yellow, Plate 4.

*Sepals.*—Smooth edge, branched. Curl back when half open.

*Calyx.*—Shape—funnel. Size—broad. Aspect—smooth.

*Peduncle.*—Length—medium. Aspect—smooth. Color—Lettuce Green, Plate 5. Strength—erect, heavy.

*Opening.*—Bud opens well. Is not affected by adverse conditions.

Bloom:

*Size.*—Large. Average size when fully expanded—4½".

*Borne.*—In irregular clusters.

*Stems.*—Medium length, strong.

*Form.*—When first open—globular. Permanence—flattens.

*Petalage.*—Double (full but open center). Number of petals under normal conditions—30.

*Color.*—Center of flower—Empire Yellow, Plate 4, near stamens blending into Begonia Rose, Plate 1, for balance of petals. Outer petals—Begonia Rose, Plate 1. Base of petals (aiglet)—Empire Yellow, Plate 4. Inside of petals—Begonia Rose, Plate 1. Reverse of petals—Pinard Yellow, Plate 4. General tonality from a distance—Pink (general color terminology).

*Discoloration.*—General tonality at end of first day—Begonia Rose, Plate 1. Second day—Eosine Pink, Plate 1.

Petals:

*Texture.*—Thick. Is not affected by hot or wet weather.

*Appearance.*—Inside—satiny. Outside—shiny.

*Form.*—Notched.

*Arrangement.*—Informal (with "rags" in center). Petaloids in center—few, small.

*Persistence.*—Drop off cleanly.

*Fragrance.*—Moderate. Nature—Tea (average Hybrid Tea scent).

*Lasting Quality.*—On the plant—long. As cut flower—short.

Genital organs:

*Stamens, Anthers.*—Medium size. Color—Deep Chrome, Plate 3. Arrangement—regular around styles mixed with petaloids.

*Stamens, filaments (threads).*—Medium length. Color—Pinard Yellow, Plate 4.
*Pollen.*—Light Orange Yellow, Plate 3.
*Styles.*—Bunched, medium length, heavy.
*Stigmas.*—Light Greenish Yellow, Plate 5.
*Ovaries.*—All enclosed in calyx.
Fruit: Variety is sterile with its own pollen.
*Form.*—Gourd shaped.
*Aspect.*—Smooth.
*Color at maturity.*—Cadmium Orange, Plate 3.
*Sepals.*—Permanent.

*Plant*

Form: Climber.
Growth: Medium vigorous, branching.
Foliage: 5 to 7 leaflets.
*Size.*—Large.
*Quantity.*—Normal.
*Color.*—New foliage: upper side, edges—Liver Brown, Plate 14; center—Cress Green, Plate 31; under side—Light Cress Green, Plate 31. Old foliage: upper side—Dark Cress Green, Plate 31; under side—Jade Green, Plate 31.
*Shape.*—Oval pointed.
*Texture.*—Upper side and under side—smooth. Ribs and veins—prominent.
*Edge.*—Serrated (saw toothed).
*Serration.*—Single, large.
*Rachis.*—Cress Green, Plate 31. Under side—smooth.
*Stipules.*—Medium length, serrated.
*Disease Resistance*—Resistant.
Wood:
*New wood.*—Color—Cress Green, Plate 31. Bark—smooth.
*Old wood.*—Color—Dark Cress Green, Plate 31. Bark—smooth.
Thorns (thorns are divided into thorns, prickles and short needles):
*Thorns.*—Quantity: on main stalks from base—few; on laterals from stalk—few. Form—narrow base, short, straight, hooked downward. Color when young—Acajon Red, Plate 13. Position—irregular.
*Prickles.*—Quantity on main stalks and on laterals—few. Color—Acajon Red, Plate 13.

What is claimed is:

A new and distinct variety of climbing Hybrid Tea Rose plant, characterized as to novelty by its hardiness, its remontant blooming habit, and the distinctive form and coloring of the flowers and foliage in the different stages of development, and the fragrance, substantially as shown and described.

FANNIE NICOLAS.
*Administratrix of the Estate of Jean H. Nicolas, Deceased.*